US006245756B1

(12) United States Patent
Patchev et al.

(10) Patent No.: US 6,245,756 B1
(45) Date of Patent: Jun. 12, 2001

(54) PHARMACEUTICAL PREPARATIONS FOR TREATMENT OF ESTROGEN DEFICIENCY IN THE CENTRAL NERVOUS SYSTEM

(75) Inventors: Vladimir Patchev; Michael Oettel; Sigfrid Schwarz, all of Jena; Ina Thieme, Graitschen; Wolfgang Roemer, Jena, all of (DE)

(73) Assignee: Jenapharm GmbH & Co. KG, Jena (DE)

( * ) Notice: Subject to any disclaimer, the term of this patent is extended or adjusted under 35 U.S.C. 154(b) by 0 days.

(21) Appl. No.: 09/252,726

(22) Filed: Feb. 19, 1999

Related U.S. Application Data
(60) Provisional application No. 60/076,192, filed on Feb. 27, 1998.

(51) Int. Cl.[7] .................... A61K 31/566; A61K 31/567

(52) U.S. Cl. .................... 514/176; 514/178; 514/179; 514/182

(58) Field of Search .................... 514/176, 178, 514/179, 182

(56) References Cited

U.S. PATENT DOCUMENTS

| | | | |
|---|---|---|---|
| 4,791,099 | 12/1988 | Aroonsakul | 514/2 |
| 4,897,389 | 1/1990 | Aroonsakul | 514/171 |
| 5,554,601 | 9/1996 | Simpkins et al. | 514/182 |

FOREIGN PATENT DOCUMENTS

| | | |
|---|---|---|
| 29741/95 | 12/1998 | (AU) . |
| 43 38 314 C1 | 3/1995 | (DE) . |
| 195 24 937 A1 | 7/1995 | (DE) . |
| WO 95/12402 | 5/1995 | (WO) . |
| WO 97/03661 | 2/1997 | (WO) . |

OTHER PUBLICATIONS

Henderson V. W., et al: :Estrogen Replacement Therapy in Older Women: Comparisons Between . . . , Arch. Neurol. 51, 896–900, 1994.
Paganini–Hill, A., et al: "Estrogen Deficiency and Risk of Alzheimer's Disease", Am. J. Epidemiol. 140, pp. 256–261, 1994.
Adan, R.A., Burbach, J. P.: "Regulations of Vasopressin and Oxatocin Gene Expression . . . ", Progr. Brain Res. 92, 127–136, 1992.
Niki, E.; Nakano, M.: "Estrogens as Antioxidants", Methods Enzymol. 186; pp. 330–333, 1990.
Lacort, M., et al: "Protective Effects of Estrogens and Catecholestrogens Against . . . ": Lipids 30, pp. 141–146, 1995.
Smith, C.D. et al: "Excess Brain Oxidation and Enzyme Dysfunction in Normal Aging . . . "; Proc. Natl. Acad. Sci. USA 88, pp. 10540–10543, 1991.
Hastings, T G; Zigmond, M.J.: :Neurodegenerate Disease and Oxidative Stress . . . ; Fiskum, G. (ed), Neurodegerative Diseases, Plenium Press, New York, pp. 37–46, 1996.
Behl, C., et al: "17B–Estradiol Protects Neurons from Oxidative Stress–Induced Cell Death in Vitro", Biochem. Biophys. Res. Comm. 216, pp. 473–482, 1995.
Bernstein, B.A., Ross, R. K. et al: "Relationship of Hormone use to Cancer Risk", J. Natl. Cancer Inst. Monograph 12, 137–147, 1992.
Knabbe, C.: Endocrine Therapy of Prostate Disease, Allolio, B, Schulte, H. M. (eds); Practical Endocrinology; Urban & Schwarzenberg, Muenchen, pp. 645–651, 1996.
Clark, J.H., et al: 'Effects of Estradiol 17B on Nuclear Occupancy of the Estragen . . . , J. Steroid. Biochem 16, pp. 323–328, 1982.
Merry, D.E. et al: "BCL–2 Gene Family in the Nervous System", Ann. rev. Neurosci. 20, pp. 245–267, 1997.
Kandouz, M., et al: "Antagonism Between Estradiol and Progestin on BCL–2 Expression . . . ", Int. J. Cancer 68, pp. 120–125, 1996.
Gould, E., et al: "Proliferation of Granule Cell Precursors in the Dentale Gyrus of . . . ", Proc. Natl. Acad. Sci. USA 96; pp. 3168–3170, 1998.
Clark, R.S S. B., et al: "Apoptosis–Suppressor Gene BCL–2 Expression After Traumatic Brain Injury in Rats";, J. Neurosci. 17, pp. 9172–9182, 1997.
Insel, T. R.: "Oxytocin, A Neuropeptide for Affiliation: Evidence From . . . ", Psychoneuroendocrinology 17, pp. 3–35, 1995.
Kremarik, P., et al: "Histoautodiographic Detection of Oxytocin–and Vasopressin–Binding Sites . . . ", J. Comp. Neurol. 333; pp. 343–359, 1993.
Patchev, V. K. et al: "Oxtyocin Binding Sites in the Art Limic and . . . ", Neuroscience 57, pp. 537–543, 1993.
Kopera, H.: "Estrogens ANSD Psychic Function", Aging and Estrogens. Front Hormone Res. 2, pp. 118–133, 1973.
Kondo, Y., et al: "Estrogen Alleviates Cognitive Dysfunction Following . . . ", Neurosci. Lett. 238, pp. 45–48, 1997.

(List continued on next page.)

Primary Examiner—Phyllis G. Spivack
(74) Attorney, Agent, or Firm—Michael J. Striker (57) ABSTRACT

Pharmaceutical preparations containing selected steroid compounds and methods of treating estrogen deficiency in the central nervous system (CNS) without influencing other organs or systems are described. These steroids have selective neurotropic estrogen-like transcription action in contrast to the systemically acting natural and synthetic estrogen compounds, such as 17α-estradiol. The selected steroids surprisingly have a selective influence on the transcription estrogen-dependent gene in the CNS and cause changes of physiological parameters as well as CNS-specific transcription effects in the dosages used with no biological effects in reproductive system tissues. They have CNS specific transcription effects at those dosages at which neither 17 β-estradiol nor 17α-estradiol had any action and the transcription estrogen-dependent gene in the CNS is not influenced by secondarily formed 17β-estradiol.

8 Claims, 7 Drawing Sheets

OTHER PUBLICATIONS

Diaz–Veliz, G., et al: "Influence of the Estrous Cycle, Ovariectomy and Estradiol Replacement . . . ", Physiol. Behav. 46, pp. 397–401, 1989.

Draft Package Insert Revised Mar. 25, 1998, Viagra, 1998 Pfizer Inc, pp. 1–18.

Netter, A.: "The Menopause", in Thibault, C., Levasseur, M.C. Hunter, R. H.F. (eds), Reproduction in Mammals and Man; Ellipses, Paris: 1993; pp. 627–643.

Van Den Beld, A. W. et al: The Role of Estrogens in Physical and Psycho–Social Well–Being in.

McEwen, B.S. et al: "Steroid Hormones as Mediators of Neuronal Plasticity", J. Steroid Biochem. Mol. Biol. 39; p. 223–232, 1991.

Fink, G.: "Gonadotropin Secretion and its Control", in Knobil, E. and Neil, J.D. (eds); The Psycology of Reproduction; Raven Press, New York, 1348–1376, 1998.

Baum, M. J., et al "Hormonal Basis of Proceptivity and Receptivity in Female Primates", Arch. Sex. Behav. 6; pp. 173–192, 1997.

Viau, V and Meaney, M. J.: "Variations in Hypothalamic-–Pituitary–Adrenal Esponse to Stress During the Estrous Cycle in the Rat", Endocrinology 129; pp. 2503–2511, 1991.

O'Neal, M. F., et al: "Estrogen Affets Performance of OV Ariectomized Rats in a Two–Choice Water–Escape Working Memory Task", Psychoneuroendocrinology 21, pp. 51–65, 1996.

Fink, G., et al: "Estrogen, Control of Central Neurotransmission: Effects on Mood, Mental State and Memory", Cell. Mol. Neurobiol. 16, pp. 325–344, 1996.

Woolley, C.S. et al: "Estradiol Mediates Fluctuations in Hippocampal Synapse Density During the Estrous Cycle in the Adult Rat"; Neurosci. 12, pp. 2549–2554, 1992.

Miranda, R. C., et al: "Presumptive Estrogen Target Neurons Express . . . "; Mol. Cell. Neurosci. 4, pp. 510–525, 1993.

Luine, V. N.: "Estradiol Increases Choline Acetyltransferase Activity . . . "; Exp. Neurol. 89, pp. 489–490, 1985.

Weiland, N.: "Glutamic Acid Decarboxlade Messenger Ribonucleic Acid . . . "; Endocrinology 131, pp. 2697–2702, 1992.

Bosse, R. and Therese Di Paolo: "The Modulation of Brain Dopamine and Gaba Receptors . . . "; Cell. Mol. Neurobiol. 16, 199–212, 1996.

Goodman, Y., et al: "Estrogens Attenuate and Corticosterone Exacerbates . . . ", J. Neurochem. 66, pp. 1836–1844, 1996.

Fig. 7
■ 17β-Estradiol (1 μg/day)
▨ 17α-Estradiol (100 μg/day)
■ prototype substance (30 μg/day)

PHARMACEUTICAL PREPARATIONS FOR TREATMENT OF ESTROGEN DEFICIENCY IN THE CENTRAL NERVOUS SYSTEM

CROSS-REFERENCE

This application claims the benefit of U.S. Provisional Patent Application, Ser. No. 60/076,192, filed Feb. 27, 1998.

BACKGROUND OF THE INVENTION

The present invention relates to a method of treating estrogen deficiency in the central nervous system without influencing other organs or systems by administration of a pharmaceutical preparation of selected steroids and to the pharmaceutical composition used in that method.

These steroids are characterized by a selective neurotropic, estrogen-like transcription action in contrast to the systematically acting natural and synthetic estrogens, including 17α-estradiol. These steroids are compounds of the general formula I:

wherein $R_1$ represents a hydrogen atom, a hydroxy group or an alkoxy group having 1 to 5 carbon atoms; $R_2$ represents a hydrogen atom, an alkyl group having 1 to 5 carbon atoms, an acyl group having 1 to 5 carbon atoms or a group of the formula $SO_2NR_{10}R_{11}$, wherein $R_{10}$ and $R_{11}$ represent, independently of each other, a hydrogen atom, an alkyl group having 1 to 5 carbon atoms, or together with nitrogen, a pyrrolidino group, a piperidino group or a morpholino group; $R_3$ represents a hydrogen atom or a hydroxy group; $R_4$ represents a hydrogen atom, a hydroxy group or an alkyl group with 1 to 5 carbon atoms; $R_5$ and $R_6$ each represent, independently of each other, a hydrogen atom or a halogen atom; $R_7$ represents hydrogen or a methyl group; $R_{8a}$ represents a hydrogen and $R_{8b}$ represents a hydroxy group or $R_{8a}$ represents a hydroxy group and $R_{8b}$ represents a hydrogen or both together represent an oxo group or a group of formula $CR_{12}R_{13}$, in which $R_{12}$ and $R_{13}$ each represent, independently of each other, a hydrogen atom or a halogen atom; $R_9$ represent a methyl or an ethyl group; Z either represents a double bond or a substituted or unsubstituted cyclopropane ring; and >$CR_5R_6$ is an a group or a β group and $R_7$ is a β group when >$CR_5R_6$ is an α group and vice versa.

An abrupt or gradual decrease of the estrogen concentrations in organisms can occur both in women and in men in various physiological conditions (increasing age, menopause) and pathological conditions (gonadectomy, use of GnRH analogs in supplemental cancer therapy). Troublesome thermoregulation in the form of hot flashes, osteoporosis and an increased predisposition to heart and circulatory illness are part of the best known clinical symptoms of estrogen deficiency (A. Netter, "The menopause", in C. Thibault, M. C. Levasseur, R. H. F. Hunter (eds.), Reproduction in Mammals and Man, Ellipses, Paris, 1993, pp. 627 to 643). The latest clinical studies (A. W. van den Beld, et al, "The Role of Estrogens in Physical and Psycho-social Well-being in Elderly Men", The Aging Male 1 (Suppl. 1), 54, 1998) definitely prove the connection between decreased serum estrogen levels and increasing aging in man. Because of that the presence and patho-physiological relevance of an "estrogen deficiency syndrome" in aging men is underscored.

The brain is a very important target organ for estrogen action. Estrogens have a decisive physiological effect on numerous neurobiological processes. Their action may be classified generally into two broad classes, organizing action and activating action (B. S. McEwen, et al, "Steroid Hormones as Mediators of Neural Plasticity", J. Steroid Biochem. Mol. Biol., 39, 223 to 232, 1991).

The first group relate primarily to the gender-specific organization of neural substrates during early ontogenesis.

The second group include specific changes in the function of neural regulatory cycles that are influenced by estrogen concentrations, which result from physiological secretion of the gonads after gender maturation. The activating effect of estrogens in the central nervous system has been reported in the following physiological processes, among others:

Gender-specific regulation of gonadotropin secretion (G. Fink, "Gonadotropin Secretion and its Control", in E. Knobil and J. D. Neil(eds.), The Physiology of Reproduction, Raven Press, New York, 1348 to 1376, 1998);

Control of Sexual Behavior (M. J. Baum, et al, "Hormonal Basis of Proceptivity and Receptivity in Female Primates", Arch. Sex. Behav. 6, 173 to 192, 1977);

Regulation of Neuroendocrine Reactions during Stress (V. Viau and M. J. Meaney, "Variations in Hypothalamic-pituitary-adrenal Response to Stress during the Estrous Cycle in the Rat", Endrocrinology 129, 2503 to 2511, 1991);

Learning and Retention of Behavioral Patterns in Adaptive Relevance (M. F. O'Neal, et al, "Estrogen Affects Performance of Ovariectomized Rats in a Two-choice Water-escape Working Memory Task", Psychoneuroendorcrinology 21, 51 to 65, 1996);

Maintenance of Reactivity of Neurochemical Mechanisms that are Indispensible for Guaranteeing Alterness and Adequate Information Processing (G. Fink, et al, "Estrogen Control of Central Neurotransmission: Effects on Mood, Mental State and Memory", Cell. Mol. Neurobiol. 16, 325 to 344, 1996);

Brain structure with Decisive Roles for Cognitive Performance and Emotional States (C. S. Wooley, B. S. McEwen, "Estradiol Mediates Fluctuations in Hippocampal Synapse Density During the Estrous Cycle in the Adult Rat", J. Neurosci. 12, 2549 to 2554, 1992);

The great neurotropic potential of estrogens finds its expression in their ability:

to induce expression of a series of central nervous system specific genes, whose products are of critical significance for the survival of nerve cells (R. C. Miranda, F. Sohrabji, C. D. Toran-Allerand, "Presumptive Estrogen Target Neurons Express mRNA for both the Neurotrophins and Neurotrophin Receptors: A Basis for Potential Development Interactions of Estrogen with the Neurotrophins", Mol. Cell. Neurosci. 4, 510 to 525, 1993);

to guarantee the variety and quality of the signal transmission in the central nervous system (V. N. Luine, "Estradiol Increases Choline Acetyltransferase Activity in Specific Basal Forebrain Nuclei and Projection Areas of Female Rates", Exp. Neurol. 89, 489 to 490, 1985); (N. Weiland, "Glutamic Acid Decarboxylase Messenger Ribonucleic Acid is Regulated by Estradiol and Progesterone in the Hippocampus", Endocrinology 131, 2697 to 2702, 1992); (R. Bossé, T. DiPaolo, "The Modulation of Brain Dopamine and $GABA_A$ Receptors by Estradiol: A Clue for CNS Changes occuring at Menopause", Cell Mol. Neurobiol. 16, 199 to 212, 1996); and to increase the resistance of nerve cells against pathological action (Y. Goodman, et al, "Estrogens Attenuate and Corticosterone Exacerbates Excitotoxicity, Oxidative Injury, and Amyloid b-peptide Toxicity in Hippocampal Neurons", J. Neurochem. 66, 1836 to 1844, 1996).

Clinical findings implicate estrogen deficiency as a causal factor in Morbus Alzheimer's pathogenicity, which maintains the clinical manifestation or progression of this disease, and point to the possiblity of estrogen replacement (V. W. Henderson, et al, "Estrogen Replacement Therapy in Older Women: Comparisons Between Alzheimer's Disease Cases and Controls", Arch. Neurol. 51, 896 to 900, 1994); (A. Paganini-Hill, V. W. Henderson,"Estrogen Deficiency and Risk of Alzheimer's Disease", Am. J. Epidemiol. 140, 256 to 261, 1994). A series of neuropeptides, whose gene transcription is influenced by physiological estrogen amounts (e.g. oxytocin and arginine vasopressin) play an important role in the control of emotional behavior components (R. A. Adan, J. P. Burbach, "Regulation of Vasopressin and Oxytocin Gene Expression by Estrogen and Thyroid Hormone", Progr. Brain Res. 92, 127 to 136, 1992).

Reports in the literature point out that estrogen deficiency is accompanied by a definite weakening of the organism's ability to eliminate reactive oxygen species and free radicals (E. Niki, M. Nakano, "Estrogens as Antioxidants", Methods Enzymol. 186, 330 to 333, 1990); (M. Lacort, et al,"Protective Effects of Estrogens and Catecholestrogens against Peroxidative Membrane Damage In Vitro", Lipids 30, 141 to 146, 1995). The excess of free radicals is implicated in mechanisms of cellular damage in many organs and systems and is connected with pathogenesis of neurodegenerative illnesses (C. D. Smith, et al, "Excess rain Protein Oxidation and Enzyme Dysfunction in Normal gain and in Alzheimer's Disease", Proc. Natl. Acad. Sci. USA 88, 10540 to 10543, 1991); (T. G. Hastings, M. J. Zigmond, "Neurodegenerate Disease and Oxidative Stress: Insights from an Animal Model of Parkinsonism" in G. Fiskum (ed), Neurodegenerate Diseases, Plenum Press, New York, 37 to 46, 1996). Also estrogen replacement assumes a role in maintaining and increasing endogenous antioxidative capacity (C. Behl, et al, "17β-Estradiol Protects Neurons from Oxidative Stress-induced Cell Death In Vitro", Biochem. Biophys. Res. Commun. 216, 473 to 482, 1995).

At the present time estrogen replacement occurs with natural and synthetic estrogens, whose action occurs in all estrogen-receptor-containing organs and systems, i.e. practically the entire body. However since these estrogens already cause great cell profileration in tissues of the female genital tract (endometrium) and breast gland epithelium, which subsequently develops into a carcinogenic differentiation, their use for therapy of symptoms of an estrogen deficiency is limited by several counter indications (B. A. Berstein, R. K. Ross, B. E. Henderson, "Relationship of Hormone Use to Cancer Risk", J. Natl. Cancer Inst. Monograph 12, 137 to 147, 1992).

The profilerative effects of estrogens involve direct risk factors for causing a benign prostate hyperplasia and/or gynecomastia in man(C. Knabbe, "Endocrine Therapy of Prostate Disease", in B. Allolio, H. M. Schulte (eds.), Practical Endocrinology, Urban & Schwarzenberg, München, 645 to 651, 1996). For this reason estrogen replacement in man, despite these known indications, has never been seriously considered.

The use of natural and synthetic estrogens with systematic action, i.e. in all organs and systems of the body, to treat neurodegenerative illnesses is claimed in the following patents: U.S. Pat. No. 4,897,389, U.S. Pat. No. 5,554,601, International Patent Documents WO 95/12402 and WO 97/03661 and German Patent Document DE 43 38 314 C1.

U.S. Pat. No. 4,897,389 protects the use of estradiol, estrone and estriol, alone or in combination with gonadotropins, androgens, anabolic androgens or human growth hormones, for treatment of senile dementia, Morbus Parkinsons, cerebral atrophy, Morbus Alzheimers, cerebellar atrophy, senile or essential tremor.

U.S. Pat. No. 5,554,601 and WO 95/12402 protects the use of estrogen substances which have slight "sexual activity" for protection of nerve cells from progressive damage and cell death, and for treatment of neurodegenerative diseases. The estrogen, 17α-estradiol, is mentioned as an example of a substance with slight "sexual activity" and neuroprotective action.

WO 97/03661 protects the use of non-estrogenic substances, which have at least two ring structures, in which at least one is a terminal phenolic ring, and whose molecular weight is less than 1000 Daltons, to guarantee neuroprotection.

German Patent Document DE 43 38 314 C1 describes steroids with a phenolic A ring structure, whose radical trapping and antioxidative properties, do not depend on the extent of their estrogen-similar activity. These compounds can be used for prophylaxis and therapy of radical-mediated cell damage.

In all these patents the therapeutic and neuroprotective efficiency of the obtained substances depends on one or more of the following end effects:

stimulation of biosynthesis of natural neuronal growth factors;

stimulation of activity of acetyl choline synthesizing enzymes or uptake of substrates of acetyl choline synthesis;

direct cytoprotection by increasing resistance of nerve-cells from the withdrawal of nutrient substrates or growth factors; and reduction of the sensitivity of nerve cells to free radicals and reactive oxygen species, which are released because of a traumatic or neurotoxic reaction.

However, none of these patents describes a steroid with selective estrogen-similar neurotropic transcription effects; i.e., those, which in a dosage in vivo, which produces no significant biological action in reproductive systems, influences the transcription of estrogen-dependent genes in the central nervous system in an estrogen-similar manner. It should be particularly emphasized that the action escribed in U.S. Pat. No. 5,554,601 and WO 95/12402 of 17α-estradiol, a substance which has a reduced estrogenicity in the genital tract (J. H. Clark, et al, "Effects of Estradiol 17α on Nuclear Occupancy of the Estrogen Receptor, Stimulation of Nuclear Type II Sites, and Uterine Growth", J. Steroid. Biochem. 16, 323 to 328, 1982), relates only to the protection of cultivated nerve cells prior to cell death induced by withdrawal of nutrient media, in which the relative potency of 17α-estradiol was not compared or evaluated together with 17β-estradiol. Moreover one concludes that a suggestion of selective neurotropic action of 17α-estradiol or its derivatives is absent from the current experimental and patent literature, while 17β-estradiol is known to have no central nervous system selectivity and thus is classified as an estrogen with systemic action. The patent WO 97/03661 and DE 43 38 314 C1 interprets the cytoprotective action of estrogens as a consequence of the radical trapping properties of its terminal phenolic A-ring. A dissociated neurotropic action of 17α-estradiol, which is based on influencing the transcription of the estrogen-sensitive genes, was neither attempted in the work disclosed in the patents nor reported in the literature.

SUMMARY OF THE INVENTION

It is an object of the present invention to provide a pharmaceutical preparation for medicinal treatment of estrogen deficiency in central nervous systems (CNS) without influencing other organs or system.

According to the invention steroids for the pharmaceutical preparation are selected which guarantee the treatment of estrogen deficiency in central nervous systems (CNS) with effecting other organs or systems.

These steroids are characterized by a selective neurotropic estrogen-similar transcription action in contrast to the systemic action of natural and synthetic estrogens, including 17α-estradiol.

It was found surprisingly that the selected steroids according to the invention
- had a selective influence on the transcription estrogen-dependent genes in CNS and cause changes of suitable physiological parameters;
- had CNS-specific transcription effects in the dosages used with no biological effects in tissues of the reproductive system;
- had CNS specific transcription effects at those dosages at which neither 17β-estradiol nor 17α-estradiol had any action; and
- the transcription estrogen-dependent gene in the CNS is not influenced by the action of secondarily formed 17β-estradiol.

These steroids of the invention are the compounds of formula I:

in which $R_1$ represents a hydrogen atom, a hydroxy group or an alkoxy group having 1 to 5 carbon atoms; $R_2$ represents a hydrogen atom, an alkyl group having 1 to 5 carbon atoms, an acyl group having 1 to 5 carbon atoms or a group of the formula $SO_2NR_{10}R_{11}$, wherein $R_{10}$ and $R_{11}$ represent, independently of each other, a hydrogen atom, an alkyl group having 1 to 5 carbon atoms or together with the nitrogen, a pyrrolidino group, a piperidino group or a morpholino group; $R_3$ represents a hydrogen atom or a hydroxy group; $R_4$ represents a hydrogen atom, a hydroxy group or an alkyl group with up to 5 carbon atoms (i.e. from 1 to 5 carbon atoms; $R_5$ and $R_6$ each represent, independently of each other, a hydrogen atom or a halogen atom; $R_7$ represents a hydrogen or methyl group; $R_8$ represents a hydrogen atom and a hydroxy group, an oxo group or a group of the general formula $CR_{12}R_{13}$, in which $R_{12}$ and $R_{13}$ each represent, independently of each other, a hydrogen atom or a halogen atom; $R_9$ represents a methyl or an ethyl group; Z represents a C,C double bond or a substituted or unsubstituted cyclopropane ring and the group $>CR_5R_6$ is arranged so that it is an α group or a β group and $R_7$ is a β group when $>CR_5C_6$ is an a group and vice versa.

Preferred compounds of formula I are:
- 15βH,3'H-cycloprop[14,15]-estra-1,3,5(10),8-tetraen-3,17α-diol,
- 15βH,3'H-cycloprop[14,15]-18α-homo-estra-1,3,5(10),8-tetraen-3,17α-diol,
- 17α-hydroxy-15βH,3'H-cycloprop[14,15]-estra-1,3,5(10),8-tetraen-3-yl-pentanoate,
- 17-methylene-15βH,3'H-cycloprop[14,15]-estra-1,3,5(10),8-tetraen-3-ol,
- 15βH,3'H-3',3'-difluoro-cycloprop[14,15]-estra-1,3,5(10),8-tetraen-3,17α-diol,
- 17-methylene-15βH,3'H-cycloprop[14,15]-estra-1,3,5(10),8-tetraen-3-yl-sulfamate,
- 17-difluoromethylen-15βH,3'H-cycloprop[14,15]-estra-1,3,5(10),8-tetraen-3-ol,
- 3-methoxy-15β-methyl-3'H-cycloprop[14,15]-estra-1,3,5(10),8-tetraen-3-ol,
- 15α-methyl-3'H-cycloprop[14,15]-estra-1,3,5(10),8-tetraen-3,17α-diol,
- 17-difluoromethylen-15βH,3'H-cycloprop[14,15]-estra-1,3,5(10),8-tetraen-3-yl-(tetramethylenimino) sulfonate, and
- 17-methylene-3'H-cycloprop[8,9]-15βH,3'H-cycloprop[14,15]-estra-1,3,5(10)-trien-3-ol.

An advantageous form of the invention is the use according to the invention of the compounds of formula I for making pharmaceutical compositions for prophylaxis and therapy of age-dependent reduction of cognitive performance, of age-conditioned and perimenopausal dysphoria, of premenstrual syndromes, of neuroses and neurasthenia, of anxiety states, of anxiety neuroses, of hot flashes after estrogen deprivation (due to menopause, gonadectomy, treament with GnRH analogs) and for psychogenic inhibition of sexual behavior. It was found that the risk of injury to or impairment of hormone sensitive tissue of the reproductive system (endometrium, myometrium, prostate, breast) in the sense of uncontrolled proliferation and carcinogenesis can be largely prevented.

The subject matter of the present invention also includes pharmaceutical preparations for oral and parenteral administration, especially for topical, rectal, subcutaneous, intravenous, intramuscular, intraperitoneal, intranasal, intravaginal, intrabuccal or sublingual administration, which contain a compound of formula I above as effective ingredient in addition to the usual carrier and diluent substances, e.g. water or gelatin.

The following are embodiments of the pharmaceutical preparations of the invention:
- tablets or pills for daily oral administration including from 0.1 to 2 mg of the effective ingredient of the invention;
- ampoules for daily subcutaneous injection including from 0.1 to 2 mg of the effective ingredient of the invention;
- plasters for transdermal release daily of from 0.05 to 2 mg of the effective ingredient of the invention;
- gels and creams for transdermal release daily of 0.05 to 2 mg of the effective ingredient of the invention; and buccal administration systems for daily release of 0.1 to 1 mg of the effective ingredient of the invention.

The medications according to the invention are provided in a suitable dosage with the conventional pharmaceutical adjuvant materials and conventional solid or liquid carriers or diluents.

In the following examples the selective estrogen-like action of a compound of the invention, namely 15βH,3'H-cycloprop[14,15]-estra-1,3,5(10),8-tetraen-3,17α-diol ($R_1=R_2=R_3=R_4=R_5=R_6=R_7$=H; $R_8$=α-OH, β-H; $R_9$=CH$_3$; Z=—C≡C—), named in connection with the figures as the prototype substance, is tested and compared with 17β-estradiol and 17α-estradiol.

BRIEF DESCRIPTION OF THE DRAWINGS

The objects, features and advantages of the invention will now be illustrated in more detail with the aid of the following description of the preferred embodiments, with reference to the accompanying figures in which.

EXAMPLES

Example 1
Effect of Chronic Subcutaneous Administration of the Prototype Substance in vivo on Uterus Weight Mature female (three months old, weight, 250±30 g) white Wistar rats (Tierzucht Schönwalde GmbH, Germany) were ovariectomized under ketamine narcosis. After 14 days the animals were implanted with an osmotic minipump (Alzett, USA), which released a daily dosage of 0.01, 0.1, 0.3, 1, 3, 30 or 100 μg of the test substance (15βH,3'H-cycloprop[14,15]-estra-1,3,5(10),8-tetraen-3,17α-diol, 17β-estradiol and 17α-estradiol) over a seven day interval. The control animal received a corresponding volume of a vehicle (propylene glycol). On the seventh treatment day the animals were sacrificed and their uterus moist weight (relative to 100 g body weight) was determined.

Figure 1:
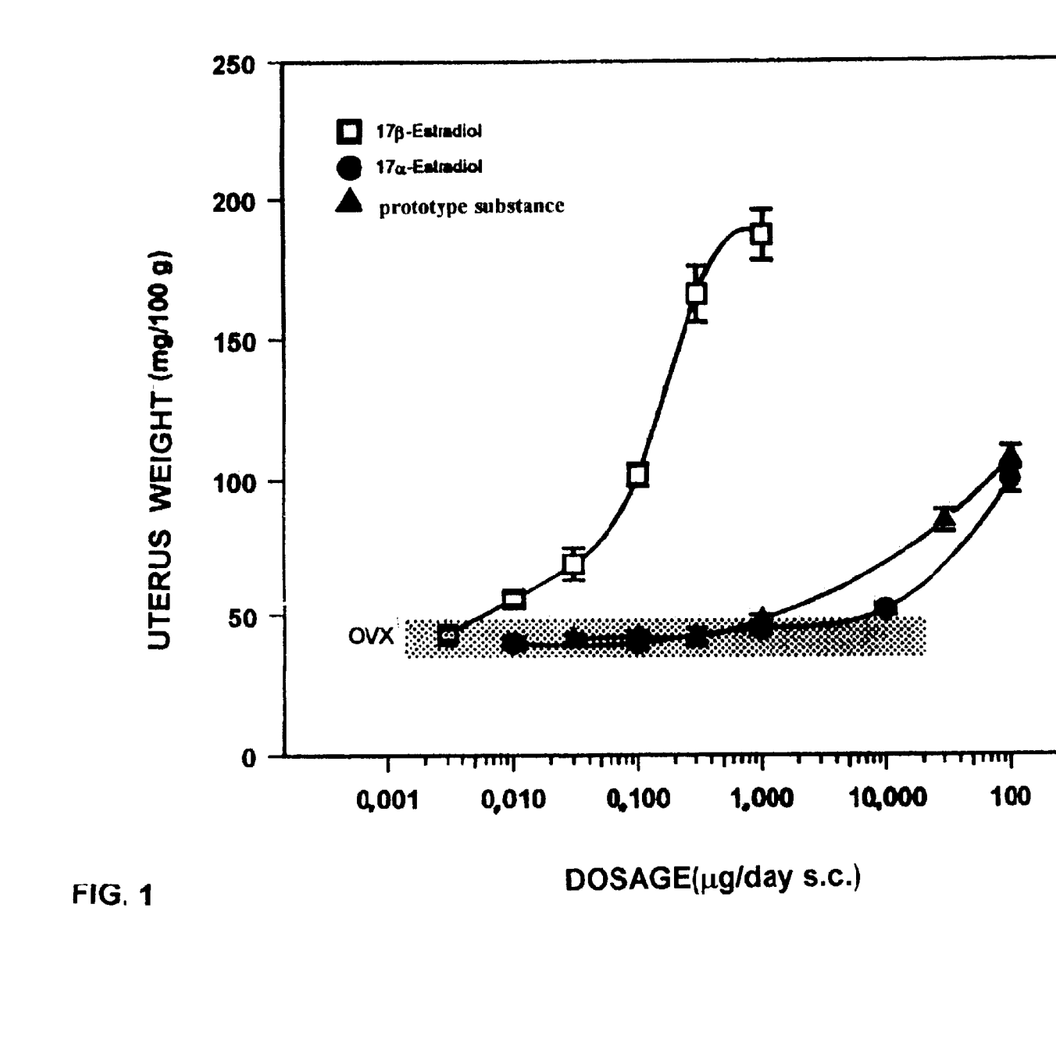
FIG. 1 is a graphical illustration comparing the uterotropic action of an example of the steroid compounds of the invention, namely 15βH,3'H-cycloprop[14,15]-estra-1,3,5(10),8-tetraen-3,17α-diol, and 17α-estradiol and 17β-estradiol.

FIG. 1 illustrates the uterotropic action of different dosages of 17β-estradiol; (rectangular symbol), 17α-estradiol (circular symbol) and 15βH,3'H-cycloprop[14,15]-estra-1,3,5(10),8-tetraen-3,17α-diol (triangular symbol) in ovariectomized rats. Each point represents the average value±standard error (x±SEM) of 7 to 10 experimental animals. The shaded area shows the scatter width of these parameters in placebo-treated animals (OVX).

It is apparent that a significant increase in the uterus already occurs with a daily dosage of from 0.03 to 0.1 μg when 17β-estradiol is administered. A daily dosage of 100 μg is required for a comparable effect when 17α-estradiol is administered. A daily dosage of 30 μg of the prototype substance, 15βH,3'H-cycloprop[14,15]-estra-1,3,5(10),8-tetraen-3,17α-diol, is required for a comparable effect when the prototype substance is administered.

Example 2
Activation of Transcription of an α-estrogen Receptor-dependent Reporter Gene in vivo Breast cancer cells MCF-7/2A, which express the alpha-isomeric form of the estrogen-receptor (Era), were transferred steadily with the receptor plasmid EREwtcLUC. The reporter contains the estrogen response element (ERE) from Vitellogenin, a thymidine kinase promotor and the Luciferase-coded gene of *Photinus pyralis*. The cell culture was cultivated for seven days prior to the start of the experiments in steroid-free medium and subsequently incubated for 48 hours with 17β-estradiol, 17α-estradiol or the prototype substance, 15βH,3'H-cycloprop[14,15]-estra-1,3,5(10),8-tetraen-3,17α-diol, in four different concentrations ($10^{-11}$, $10^{-10}$, $10^{-9}$, $10^{-8}$ M). The cells were made lytic and the transcription of the Luciferase reporter gene was measured to determine the Luciferase activity with a specific test substance (Serva/Promega, Germany).

Figure 2:
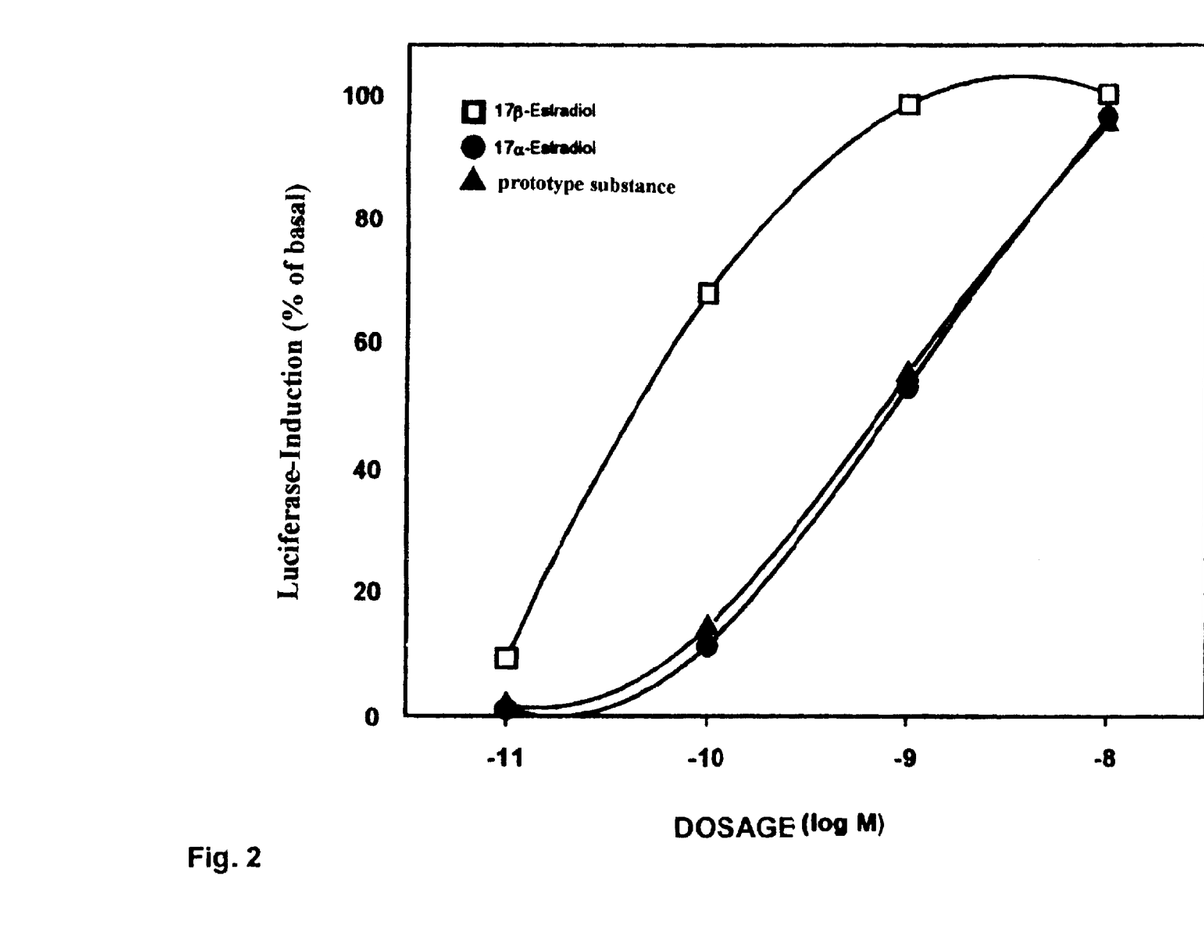
FIG. 2 is a graphical illustration showing the induction of the transcription of a stable transferred reporter gene (Luciferase) in estrogen receptor breast cancer cells with the same steroid compounds as in FIG. 1.

FIG. 2 shows the induction of the transcription of a stable transferred reporter gene (Luciferase) in estrogen receptor breast cancer cells MCF-7 after 48 hour treatment with different dosages of 17β-estradiol (rectangular symbol), 17α-estradiol (circular symbol) and 15βH,3'H-cycloprop[14,15]-estra-1,3,5(10),8-tetraen-3,17α-diol (triangular symbol). The figure shows the average value of two independent experiments.

It is apparent that the tested substances stimulate the transcription of the reporter in a dosage-dependent manner. The efficiency of the 15βH,3'H-cycloprop[14,15]-estra-1,3,5(10),8-tetraen-3,17α-diol and 17α-estradiol is an order of magnitude (i.e. 10-fold) less than that of 17β-estradiol. This result shows that the prototype substance, 15βH,3'H-cycloprop[14,15]-estra-1,3,5(10),8-tetraen-3,17α-diol, has a many times weaker estrogen action in breast cancer tissue.

Example 3
Stimulation of the Transcription of Oxytocin Gene in Brain After Chronic Treatment in vivo with Dosages that are Ineffective in the Uterus Mature female (three months old, weight, 250±30 g) white Wistar rats (Tierzucht Schönwalde GmbH, Germany) were ovarectomized under ketamine narcosis. After 14 days the animals were implanted with an osmotic minipump (Alzett, USA), which released a daily dosage of 0.01, 0.1 or 1 μg of test substance (15βH,3'H-cycloprop[14,15]-estra-1,3,5(10),8-tetraen-3,17α-diol, 17β-estradiol and 17α- estradiol) over a seven day interval. The control animal received a corresponding volume of a vehicle (propylene glycol). On the seventh treatment day the animals were sacrificed and their uterus moist weight (relative to 100 g body weight) was determined. The messenger ribonucleic acid (mRNA) that codes the biosynthesis of oxytocin was produced by in-situ-hybridization with a specific radioactive-marked oligodeoxynucleotide probe according to methods established in hypothalamic Nucleus paraventricularis (PVN) (D. Fischer, et al, "Lactation as a Model of Naturally Reversible Hypercorticalism: Plasticity in the Mechanism Governing Hypothalamo-pituitary-adrenal Activity in the Rat", J. Clin. Invest. 96, 1208 to 1215, 1995). Treatment-conditioned changes in the transcription of the oxytocin gene were quantified by densitometric measurements of specific hybridization signals within definite anatomical structures.

Figure 3A:
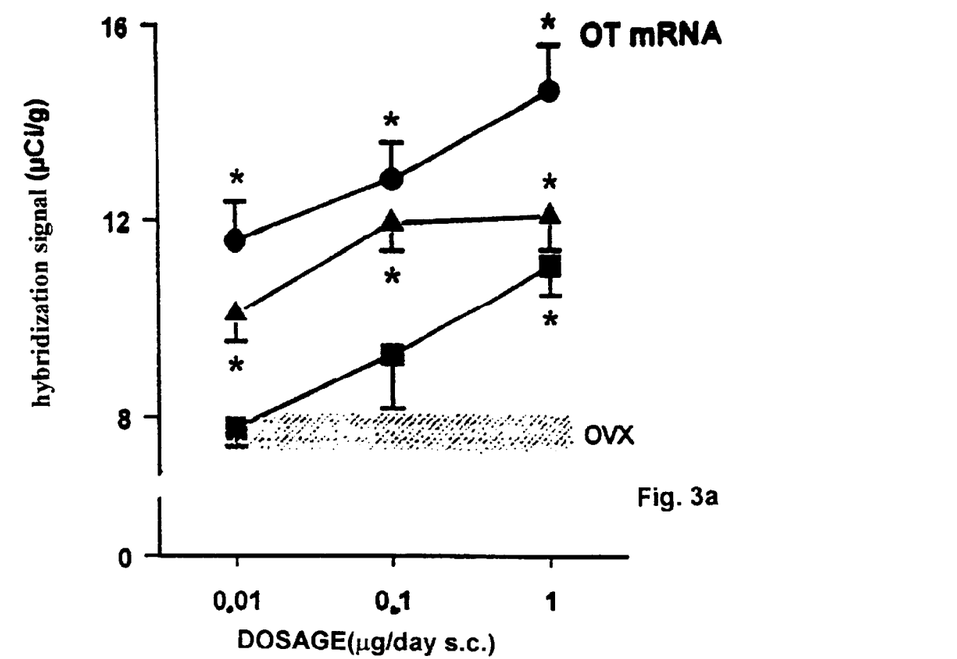
FIGS. 3a and 3b are graphical illustrations showing the induction of OT mRNA in hypothalamic paraventricular Nuclear ovarectomized rats and the uterus weight respectively after chronic subcutaneous treatment with the same steroid compounds as in FIG. 1.
Figure 3B:
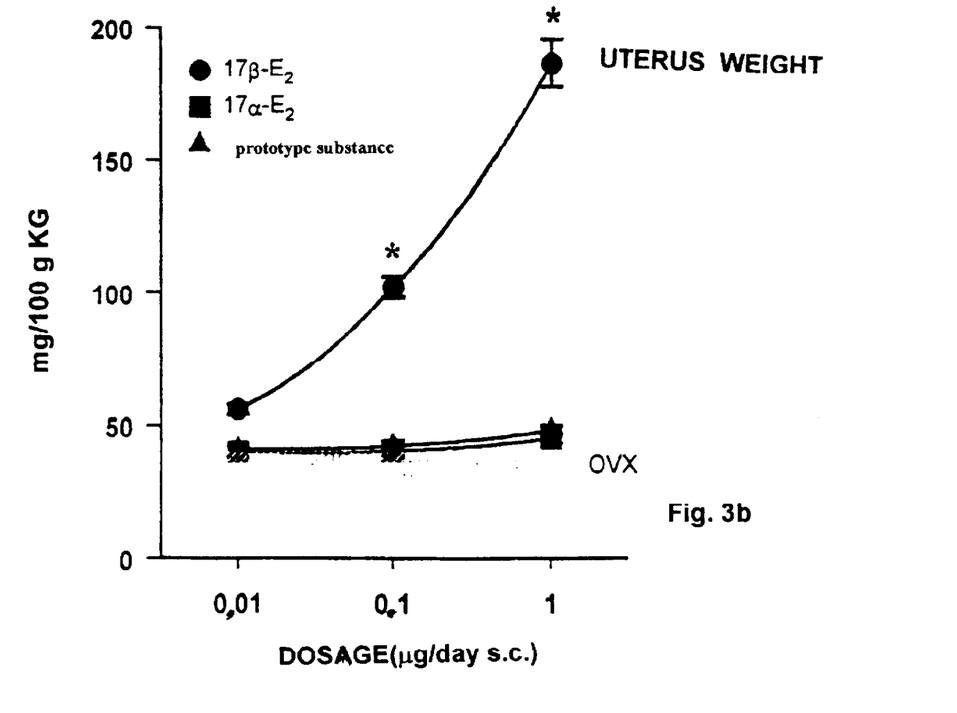

FIGS. 3a shows the induction of oxytocin-coded transcriptens (OT mRNA; upper illustration) in hypothalamic paraventricular Nuclear ovariectomized rats after chronic subcutaneous treatment with 17β-estradiol (circular symbols), 17β-estradiol (rectangular symbols) and 15βH, 3'H-cycloprop[14,15]-estra-1,3,5(10),8-tetraen-3,17α-diol (triangular symbols) in three different dosages. The lower illustration, FIG. 3b, shows the effects of the tested substances on the uterus weight. Each point represents x±SEM of 5 to 7 individual measurements. The shaded area shows the scatter width of the corresponding parameters in the vehicle-treated rats. The star symbol indicates significant differences (p<0.05) compared to the control group (OVX).

The results show that 15βH,3'H-cycloprop[14,15]-estra-1,3,5(10),8-tetraen-3,17α-diol stimulates the transcription of oxytocin gene in PVN in a dosage-dependent manner. The stimulation effect of 17β-estradiol is very similar. Generally the neurotropic transcription effects of 15βH,3'H-cycloprop[14,15]-estra-1,3,5(10),8-tetraen-3,17α-diol are quite different from 17β-estradiol with no uterus enlargement. In the dosages used 17α-estradiol has no effect on the concentrations of oxytocin-mRNA in hypothalamic PVN.

These results document a selective estrogen-like action of 15βH,3'H-cycloprop[14,15]-estra-1,3,5(10),8-tetraen-3,17α-diol in the brain of white rats.

Example 4

Stimulation of the Transcription of Antiapoptotic Gene Bcl-2 in Hippocampus After Chronic Treatment in vivo with Dosages that Have No Uterotropic Action The experimental material originated from animals that were treated as in Example 3. The gene bcl-2 codes the synthesis of a protein that is involved in the cascade of cell proliferation and acts against the programming of cell death (apoptosis) (D. E. Merry, S. J. Korsmeyer, "Bcl-2 Gene Family in the Nervous System", Ann. Rev. Neurosci. 20, 245–267, 1997). The transcription of the gene is stimulated by estrogens (M. Kandouz, et al, "Antagonism between Estradiol and Progestin on Bcl-2 Expression in Breast Cancer Cells", Int. J. Cancer 68, 120 to 125, 1996). Gyrus Dentatus is a component of the hippocampal formation, in which the neurogenesis persists in rats, also in those becoming senile (E. Gould, et al, "Profileration of Granule Cell Precursors in the Dentate Gyrus of Adult Monkeys is Diminished by Stress" Proc. Natl. Acad. Sci. USA 96, 3168 to 3170, 1998) and bcl-2 is expressed. Bcl-2 transcripts were produced by in-situ-hybridization with a specific oligonucleotide probe (R. S. B. Clark, et al, "Apoptosis-suppressor Gene Bcl-2 Expression after Traumatic Brain Injury in Rats", J. Neurosci. 17, 1997, pp. 9172 to 9182), and quantified according to the densometric method described in example 3.

Figure 4A:
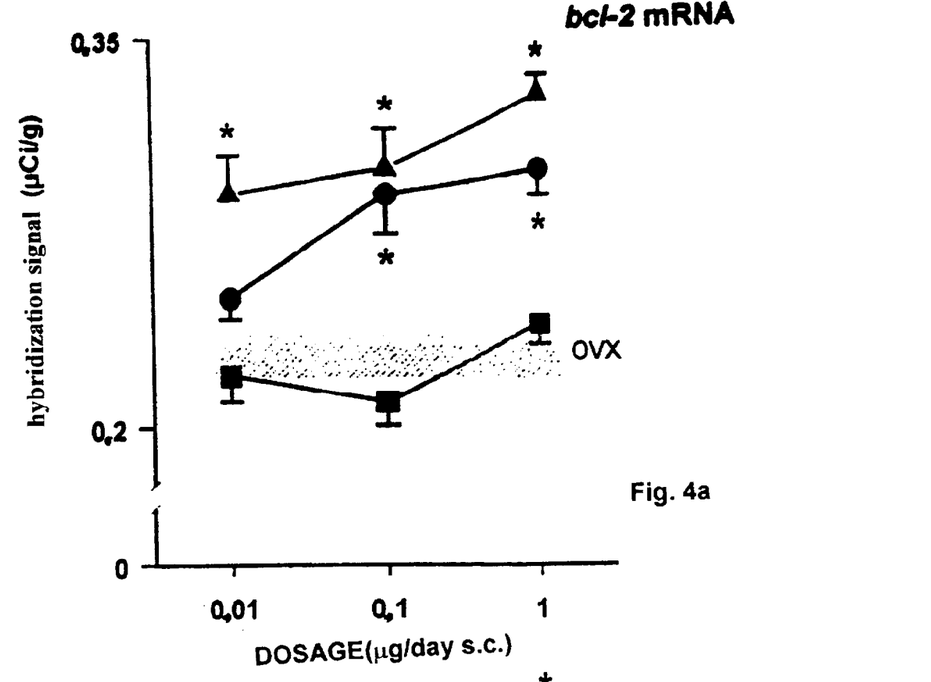
FIGS. 4a and 4b are graphical illustrations showing the effect of three different dosages of the same steroid compounds as in FIG. 1 on the expression of bcl-2 in Gyrus dentatus of the hippocampus of ovariectomized rats and the uterus weight respectively.
Figure 4B:
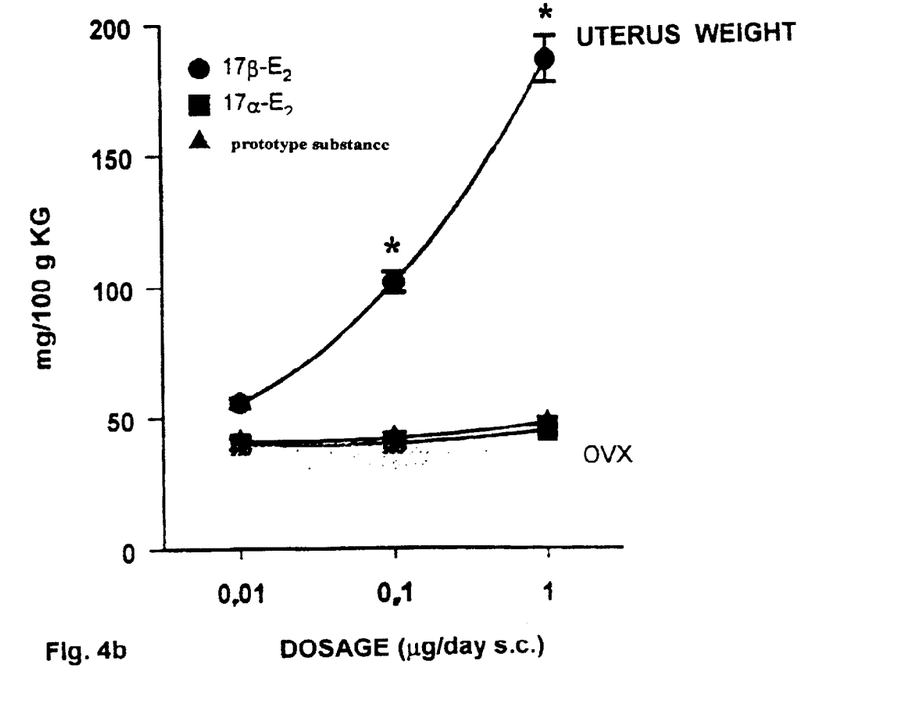

FIGS. 4a and 4b illustrate the effect of three different dosages of 15βH,3'H-cycloprop[14,15]-estra-1,3,5(10),8-tetraen-3,17α-diol (triangular symbols), 17β-estradiol (circular symbols) and 17α-estradiol (rectangular symbols) on the expression of bcl-2 in Gyrus dentatus of the hippocampus of ovariectomized rats; reference characters and abbreviations are the same as in FIGS. 3a and 3b.

The treatment with the substance 15βH,3'H-cycloprop[14,15]-estra-1,3,5(10),8-tetraen-3,17α-diol resulted in a dosage-dependent stimulation of expression of bcl-2 in Gyrus dentatus. The effect was the same as that which was produced by the same dosage of 17β-estradiol. The substance 17α-estradiol had no effect on the transcription of bcl-2 in the different dosages, apparently from FIG. 4. These results show that 15βH,3'H-cycloprop[14,15]-estra-1,3,5(10),8-tetraen-3,17α-diol influences the transcription of the antiapoptotic gene bcl-2 in the central nervous system in an estrogen-like manner in the dosages used, without acting on the uterus.

Example 5

Dissociative Induction of Oxytocin-receptors in Brain and in Myomrtrium

Binding sites with identical biochemical characteristics for the peptide hormone oxytocin are present in myometrium and in the central nervous system. In both organs acute or chronic estrogen treatment causes an increase in the number (density) of oxytocin receptors. The brain structures, in which these parameters are particularly sensitively effected by estrogens, are the Nucleus interstitialis striae terminalis, Nucleus ventromedialis and the amygdaloid Nuclear complex. Estrogen-conditioned induction of oxytocin receptors in these structures causes the expression of a series of prosocial behavior patterns, also sexual behavior (T. R. Insel, "Oxytocin, a Neuropeptide for Affiliation: Evidence from Behavioral, Receptor Autoradiographic, and Comparative Studies", Psychoneuro-endocrinology 17, 3 to 35, 1992).

The autoradiographic representation by binding of radioactive marked oxytocin-receptor antagonists $d(CH_2)_5$-Try $(Me)^2$, $Thr^4$, $Orn^8$-$[^{125}I]Tyr^9$-Vasotocin ($^{125}I$-OVTA) is the method of choice to determine the density of oxytocin receptors in defined anatomical structures (P. Kremarik, et al, "Histoautoradiographic Detection of Oxytocin- and Vasopressin-binding sites in the Telencephalon of the Rat", J. Comp. Neurol. 333, 343 to 359, 1993). Frozen sections of brain and uterus of ovariectomized rats, which were given (compare example 3) a daily subcutaneous dosage of 1 μg of 15βH,3'H-cycloprop[14,15]-estra-1,3,5(10),8-tetraen-3, 17α-diol, 17β-estradiol or 17α-estradiol for seven days, were incubated with $^{125}I$-OVTA (NEN DuPont, Germany) in a concentration of 50 pM. Subsequently film autoradiograms were prepared, which were used for densitometric determination of the oxytocin binding sites according to the established methods (V. K. Patchev, et al, "Oxytocin Binding Sites in Rat Limbic and Hypothalamic Structures: Site-specific Modulation by Adrenal and Gonadal Steroids", Neurosince 57, 537 to 543, 1993).

Figure 5A:
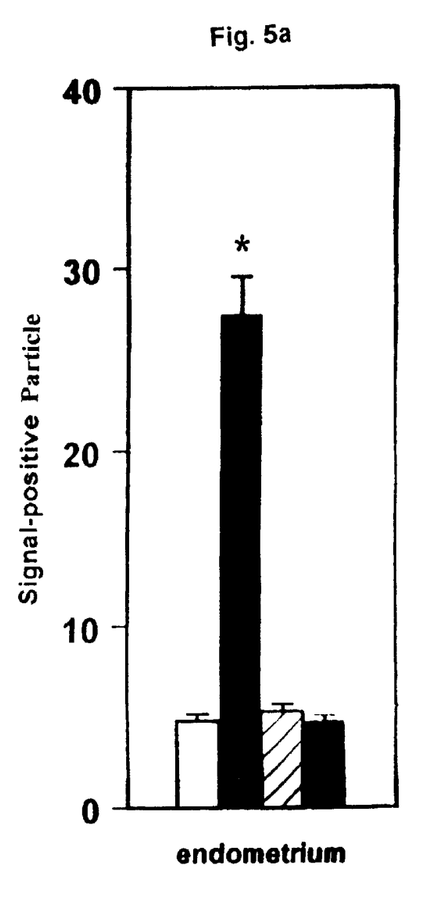
FIGS. 5a and 5b are graphical illustrations showing the specific binding of an $^{125}$I marked ligand of the oxytocin receptor ($^{125}$I-OVTA) in myometrium and in two estrogen-sensitive brain structures after treatment with the same steroid compounds as in FIG. 1.
Figure 5B:
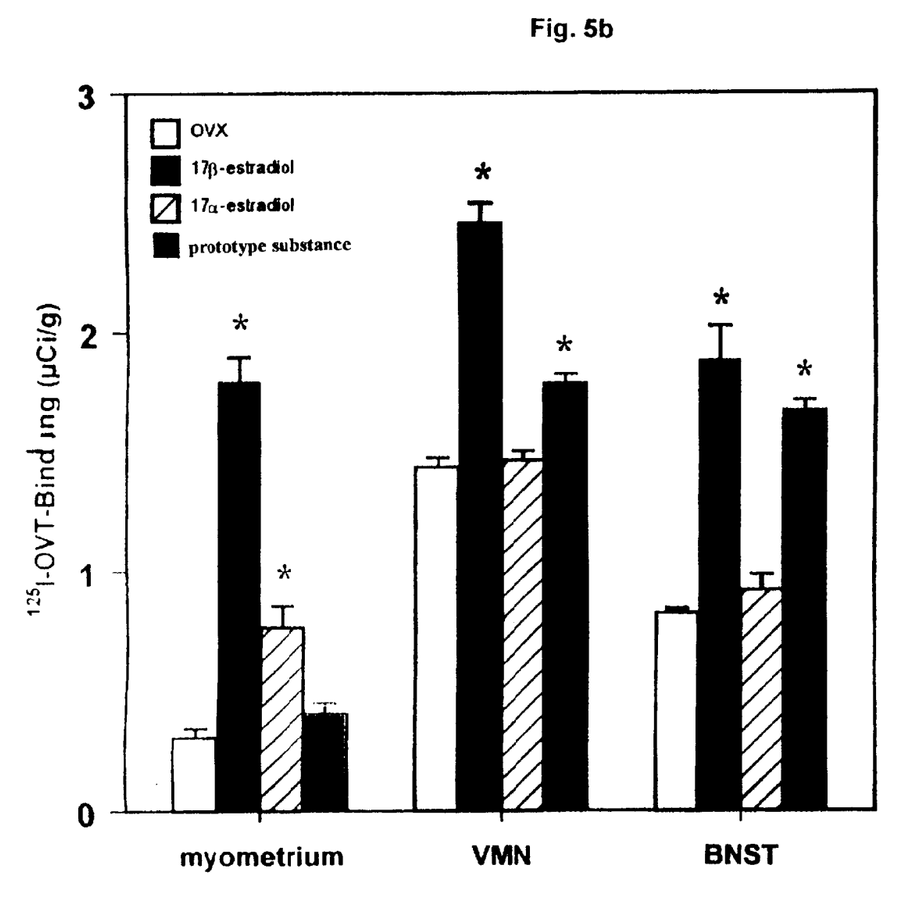

FIGS. 5a and 5b show the specific binding of an $^{125}I$ marked ligand of the oxytocin receptor ($^{125}I$-OVTA) in myometrium and in two estrogen-sensitive brain structures, the hypothalamic ventromedial Nucleus (VMN) and the Nucleus interstitialis striae terminalis (BNST), after a seven day treatment with 17β-estradiol (black column), 17β-estradiol (shaded column) and 15βH,3'H-cycloprop[14,15]-estra-1,3,5(10),8-tetraen-3,17α-diol (gray column) at a daily dosage of 1 μg. The stars indicate significant differences (p<0.05) compared to placebo-treated ovariectomized rats (OVX). The right graphical illustration (FIG. 5a) illustrates the effect of the tested substances on the proliferation of the endometrium. Each column represents x±SEM of four to five individual determinations.

The results of these experiments are similarly shown in FIGS. 5a and 5b. The treatment with 17β-estradiol and 15βH,3'H-cycloprop[14,15]-estra-1,3,5(10),8-tetraen-3,17α-diol resulted in a significant increase in the density of oxytocin receptors in all treated brain structures. However 15βH,3'H-cycloprop[14,15]-estra-1,3,5(10),8-tetraen-3,17α-diol produced a weaker effect than 17β-estradiol in VMN. The substance 17α-estradiol was effective in no brain structure at the dosages used. In myometrium 17β-estradiol caused a strong induction of oxytocin binding sites, while 17β-estradiol and the substance 15βH,3'H-cycloprop[14,15]-estra-1,3,5(10),8-tetraen-3,17α-diol produced a significantly smaller effect. The computer-assisted measurement of the strength of the endometrium in the uterus prepartion showed that the daily dosage of 1 μg caused a significant endometrial proliferation, while 15βH,3'H-cycloprop[14,15]-estra-1,3,5(10),8-tetraen-3,17α-diol did not influence the strength of the endometrium at an equivalent dosage. In summary the results in example 5 showed that the substance 15βH,3'H-cycloprop[14,15]-estra-1,3,5(10),8-tetraen-3,17α-diol influences a biochemical parameter, the oxytocin receptor which is characteristic for the reproductive system (myometrium) and for the central nervous system, predominantly in the central nervous system and differs qualitatively from the natural estrogens, 17α-estradiol and 17β-estradiol, because of its selective neurotropic action.

Example 6
Effect on Cognative Functions After Chronic Treatment

It is known that a reduction of the estrogen concentrations is associated with a reduction in learning and thinking abilities (H. Kopera, "Aging and Estrogens", Front Hormone Res. 2, 118 to 133, 1973). A correlation between serum estrogen level and cognitive performance was proven also in animal model studies (Y. Kondo, K. Suzuki, Y.Sakuma, "Estrogen Alleviates Cognitive Dysfunction Following Transient Brain Ischemia in Ovariectomized Gerbils", Neurosci. Lett. 238, 45 to 48, 1997). To compare the effect of the substances, 15βH,3'H-cycloprop[14,15]-estra-1,3,5(10),8-tetraen-3,17α-diol, 17β-estradiol and 17α-estradiol, on cognitive performance the following experiment was performed.

Mature female white Wistar rats (weight 240±20 g) were ovariectomized under nembutal narcosis. A week after the operation daily subcutaneous administration of the following daily dosages was begun: 15βH,3'H-cycloprop[14,15]-estra-1,3,5(10),8-tetraen-3,17α-diol, 30 μg; 17β-estradiol, 1 μg and 17α-estradiol, 100 μg. The entire treatment time was 14 days. On the fifth and sixth treatment day training to learn a conditioned escape behavior was performed according to established methods (G. Diaz-Veliz, et al, "Influence of the Estrous Cycle, Ovariectomy and Estradiol Replacement upon the Acquisition of Conditioned Avoidance Responses in Rats", Physiol. Behav. 46, 397 to 401, 1989). Each animal was exposed in a session to an unconditioned stimuli (electric shock) and two conditioning stimuli (light and sound signal). On the seventh treatment day the retention of the learned behavior pattern was tested. After a 6 day interruption of the learning sessions, the extinction of the learned conditioned behavior was measured on the 14th treatment day. The number of correct behavioral reactions (escape in the "safe" section of the apparatus inside of three seconds after presentation of the conditioning signal) from fifth successive exposures was used as a criterion for the evaluation of the retention or extinction of the learned behavior.

Figure 6:
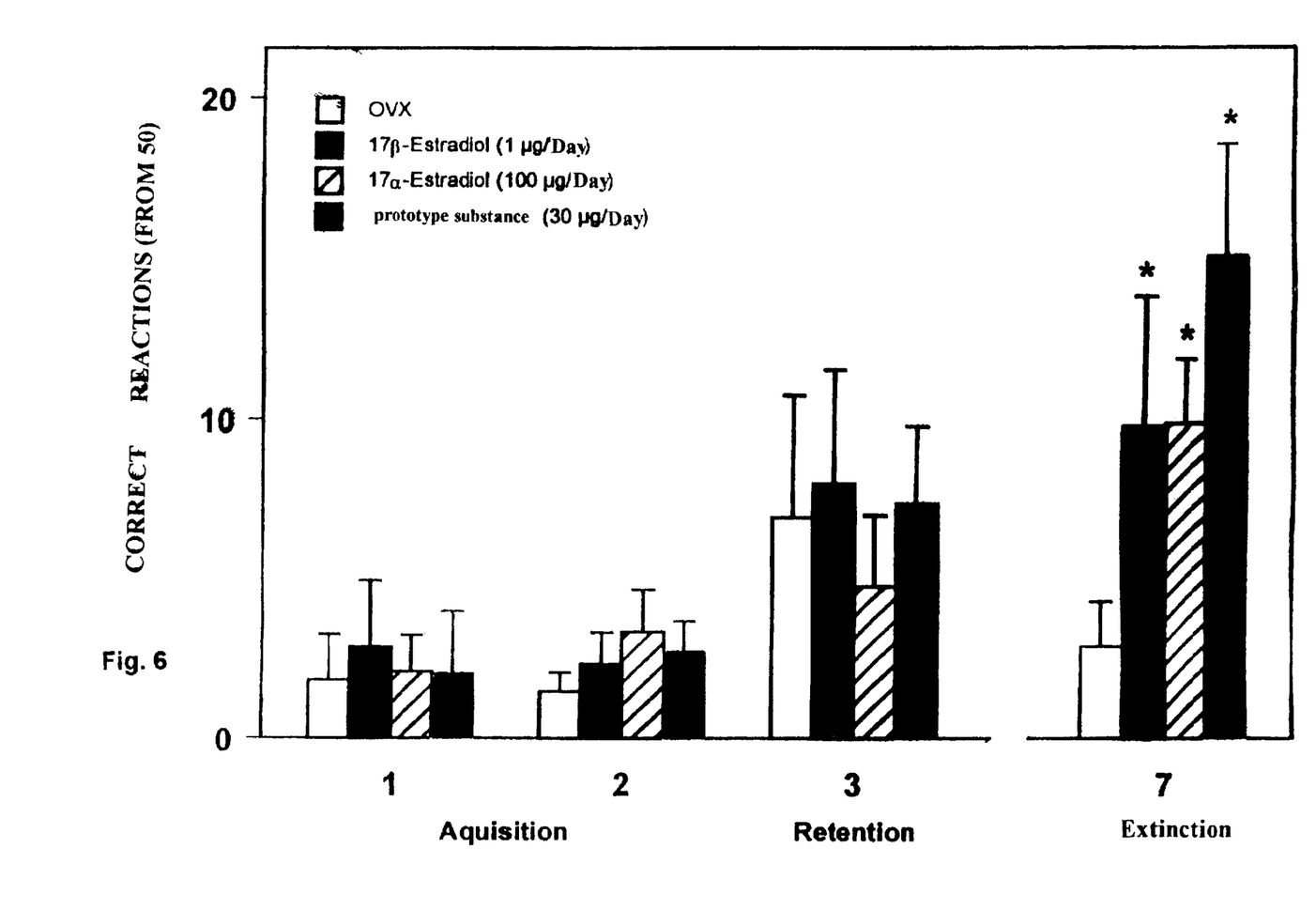
FIG. 6 is a graphical illustration showing the effect of the same steroids compounds as in FIG. 1, namely 17β-estradiol, 17α-estradiol and 15βH,3'H-cycloprop[14,15]-estra-1,3,5(10),8-tetraen-3,17α-diol, on the acquisition and retention of a new behavior pattern in ovariectomized rats.

FIG. 6 shows the effect of 17β-estradiol (black columns), 17α-estradiol (shaded column) and 15βH,3'H-cycloprop[14,15]-estra-1,3,5(10),8-tetraen-3,17α-diol (gray column) on the acquisition and retention of a new behavior pattern in ovariectomized rats (open column; OVX). The stars show significant differences in comparison to the placebo-treated animals (OVX) on the corresponding test day. The following uterus weight (x±SEM; n=8 to 10 per treatment group; given in mg/100 g KG) was measured after 14 day treatment: OVX, 53±2; 17β-estradiol, 187±9; 17α-estradiol, 100±5; and 15βH,3'H-cycloprop[14,15]-estra-1,3,5(10),8-tetraen-3,17α-diol, 108±4.

It is apparent that the substance 15βH,3'H-cycloprop[14,15]-estra-1,3,5(10),8-tetraen-3,17α-diol had an estrogen-like stimulating effect on the retention of the learned behavior pattern in the dosage used, whereas the uterotropic action is significantly smaller than that of 17β-estradiol at a daily dosage of 1 μg. This result shows that 15βH,3'H-cycloprop[14,15]-estra-1,3,5(10),8-tetraen-3,17α-diol influences the cognitive performance like an estrogen while producing only slight proliferative action in the reproductive organs.

Example 7
Biotransformation of 17α-hydroxy-14, 15α-methylene-estra-3,5,(10)8-tetraen-3-ol and 17α-estradiol to 17β-estradiol Ovariectomized rats were given daily subcutaneous doses of 100 μg of 17α-estradiol; 30 μg of 15βH,3'H-cycloprop[14,15]-estra-1,3,5(10),8-tetraen-3,17α-diol; or 1 μg of 17β-estradiol (see Example 6). The serum concentration of 17β-estradiol was measured in the three experimental groups on the last treatment day and compared with that of a vehicle-treated control.

Figure 7:
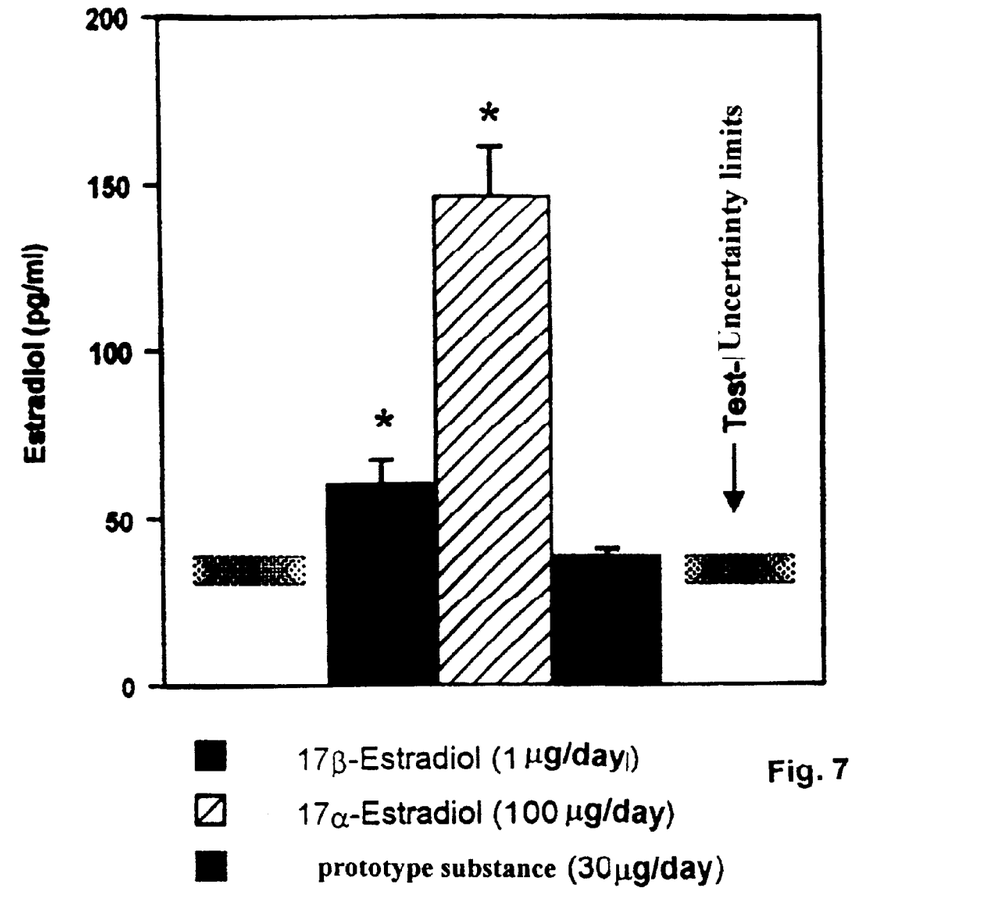
FIG. 7 is a graphical illustration showing comparative results of measurements of the biotransformation of 17α-hydroxy-14,15α-methylene-estra-3,5,(10)8-tetraen-3-ol and 17α-estradiol to 17β-estradiol.

FIG. 7 shows the serum values of 17β-estradiol after a seven day subcutaneous treatment of ovariectomized rats with 17β-estradiol (black column), 17β-estradiol (shaded column) and 15βH,3'H-cycloprop[14,15]-estra-1,3,5(10),8-tetraen-3,17α-diol (gray column) in the indicated dosages. The stars indicate significant differences in comparison to the values which were measured in the placebo-treated animals; the latter were under the uncertainty limits of the methods; each treatment group consisted of seven animals.

It is apparent that measurable concentrations of 17β-estradiol were found in the serum after administration of 17α-estradiol and 17β-estradiol in the above-mentioned dosages. Chronic subcutaneous treatment with 15βH,3'H-cycloprop[14,15]-estra-1,3,5(10),8-tetraen-3,17α-diol caused no increase in the endogenous 17β-estradiol level. This results shows that the observed pharmacological effects after administration of 15H,3'H-cycloprop[14,15]-estra-1,3,5(10),8-tetraen-3,17α-diol do not include a biotransformation of that substance to 17β-estradiol.

While the invention has been illustrated and described as embodied in pharmaceutical preparations for treatment of estrogen deficiency in the central nervous system, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

1. A method of treating estrogen deficiency in the central nervous system of a man or an animal, said method comprising administering an effective amount of a steroid compound having a selective neurotropic transcription action in contrast to a systemic action like that of estrogen compounds, wherein said steroid compound is a compound of formula I:

wherein $R_1$ represents a hydrogen atom, a hydroxy group or an alkoxy group having 1 to 5 carbon atoms; $R_2$ represents a hydrogen atom, an alkyl group having 1 to 5 carbon atoms, an acyl group having 1 to 5 carbon atoms or a group of the formula $SO_2NR_{10}R_{11}$, wherein $R_{10}$ and $R_{11}$ represent, independently of each other, a hydrogen atom, an alkyl group having 1 to 5 carbon atoms, or together with nitrogen, a pyrrolidino group, a piperidino group or a morpholino group;

$R_3$ represents a hydrogen atom or a hydroxy group; $R_4$ represents a hydrogen atom, a hydroxy group or an alkyl group with 1 to 5 carbon atoms; $R_5$ and $R_6$ each represent, independently of each other, a hydrogen atom or a halogen atom; $R_7$ represents hydrogen or a methyl group; $R_{8a}$ represents a hydrogen and $R_{8b}$ represents a hydroxy group or $R_{8a}$ represents a hydroxy group and $R_{8b}$ represents a hydrogen or $R_{8a}$ and $R_{8b}$ together represent an oxo group or a group of formula $CR_{12}R_{13}$, in which $R_{12}$ and $R_{13}$ each represent, independently of each other, a hydrogen atom or a halogen atom; $R_9$ represent a methyl or an ethyl group; Z either represents a double bond or a substituted or unsubstituted cyclopropane ring; and $>CR_5R_6$ is an α group or a β group and $R_7$ is a β group when $>CR_5R_6$ is an α group and vice versa; and a pharmaceutically acceptable carrier and/or diluent.

2. A method of treating estrogen deficiency in the central nervous system of a man or an animal, said method comprising administering an effective amount of a steroid compound selected from the group consisting of 15βH,3'H-cycloprop[14,15]-estra-1,3,5(10),8-tetraen-3,17α-diol, 15βH,3'H-cycloprop[14,15]-18α-homoestra-1,3,5(10),8-tetraen-3,17α-diol, 17α-hydroxy-15βH,3'H-cycloprop[14,15]-estra-1,3,5(10),8-tetraen-3-yl-pentanoate, 17-methylene-15βH,3'H-cycloprop[14,15]-estra-1,3,5(10),8-tetraen-3-ol, 15βH,3'H-3',3'-difluorocycloprop[14,15]-estra-1,3,5(10),8-tetraen-3,17α-diol, 17-methylene-15βH,3'H-cycloprop[14,15]-estra-1,3,5(10),8-tetraen-3-yl-sulfamate, 17-difluoromethylene-15βH,3'H-cycloprop[14,15]-estra-1,3,5(10),8-tetraen-3-ol, 3-methoxy-15β-methyl-3'H-cycloprop[14,15]-estra-1,3,5(10),8-tetraen-3-ol, 15α-methyl-3'H-cycloprop[14,15]-estra-1,3,5(10),8-tetraen-3,17α-diol,

17-difluoromethylene-15βH,3'H-cycloprop[14,15]-estra-1,3,5(10),8-tetraen-3-yl-(tetramethylenimino)sulfonate and 17-methylene-3'H-cycloprop[8,9]-15βH,3'H-cycloprop[14,15]-estra-1,3,5(10)-trien-3-ol;

and a pharmaceutically acceptable carrier and/or diluent;

wherein said steroid compound has a selective neurotropic transcription action in contrast to a systemic action like that of estrogens.

3. A method of treating conditions characterized by estrogen deficiency selected from the group consisting of age-dependent reduction of cognitive performance, of age-conditioned and perimenopausal dysphoria, of premenstrual syndromes, of neuroses and neurasthenia, of anxiety states, of anxiety neuroses, of hot flashes after estrogen-deficiency caused by menopause, gonadectomy and treatment with GnRH analogs as well as psychogenic inhibition of sexual performance, said method comprising administering an effective amount of a steroid compound having a selective neurotropic transcription action in contrast to a systemic action like that of estrogen compounds, wherein said steroid compound is a compound of formula I:

wherein $R_1$ represents a hydrogen atom, a hydroxy group or an alkoxy group having 1 to 5 carbon atoms; $R_2$ represents a hydrogen atom, an alkyl group having 1 to 5 carbon atoms, an acyl group having 1 to 5 carbon atoms or a group of the formula $SO_2NR_{10}R_{11}$, wherein $R_{10}$ and $R_{11}$ represent, independently of each other, a hydrogen atom, an alkyl group having 1 to 5 carbon atoms, or together with nitrogen, a pyrrolidino group, a piperidino group or a morpholino group;

$R_3$ represents a hydrogen atom or a hydroxy group; $R_4$ represents a hydrogen atom, a hydroxy group or an alkyl group with 1 to 5 carbon atoms; $R_5$ and $R_6$ each represent, independently of each other, a hydrogen atom or a halogen atom; $R_7$ represents hydrogen or a methyl group; $R_{8a}$ represents a hydrogen and $R_{8b}$ represents a hydroxy group or $R_{8a}$ represents a hydroxy group and $R_{8b}$ represents a hydrogen or $R_{8a}$ and $R_{8b}$ together represent an oxo group or a group of formula $CR_{12}R_{13}$, in which $R_{12}$ and $R_{13}$ each represent, independently of each other, a hydrogen atom or a halogen atom; $R_9$ represent a methyl or an ethyl group; Z either represents a double bond or a substituted or unsubstituted cyclopropane ring; and $>CR_5R_6$ is an α group or a β group and $R_7$ is a β group when $>CR_5R_6$ is an α group and vice versa; and a pharmaceutically acceptable carrier and/or diluent.

4. The method according to claim 3, wherein said effective amount is from 0.05 to 2 μg and said administering occurs once a day.

5. A method of treating conditions characterized by estrogen deficiency selected from the group consisting of age-dependent reduction of cognitive performance, of age-conditioned and perimenopausal dysphoria, of premenstrual syndromes, of neuroses and neurasthenia, of anxiety states, of anxiety neuroses, of hot flashes after estrogen-deficiency caused by menopause, gonadectomy and treatment with GnRH analogs as well as psychogenic inhibition of sexual performance, said method comprising administering an effective amount of a steroid compound selected from the group consisting of 15βH,3'H-cycloprop[14,15]-estra-1,3,5(10),8-tetraen-3,17α-diol, 15βH,3'H-cycloprop[14,15]-18α-homoestra-1,3,5(10),8-tetraen-3,17α-diol, 17α-hydroxy-15βH,3'H-cycloprop[14,15]-estra-1,3,5(10),8-tetraen-3-yl-pentanoate, 17-methylene-15βH,3'H-cycloprop[14,15]-estra-1,3,5(10),8-tetraen-3-ol, 15βH,3'H-3',3'-difluorocycloprop[14,15]-estra-1,3,5(10),8-tetraen-3,17α-diol, 17-methylene-15βH,3'H-cycloprop[14,15]-estra-1,3,5(10),8-tetraen-3-yl-sulfamate, 17-difluoromethylene-15βH,3'H-cycloprop[14,15]-estra-1,3,5(10),8-tetraen-3-ol, 3-methoxy-15β-methyl-3'H-cycloprop[14,15]-estra-1,3,5(10),8-tetraen-3-ol, 15α-methyl-3'H-cycloprop[14,15]-estra-1,3,5(10),8-tetraen-3,17α-diol, 17-difluoromethylene-15βH,3'H-cycloprop[14,15]-estra-1,3,5(10),8-tetraen-3-yl-(tetramethylenimino)sulfonate and 17-methylene-3'H-cycloprop[8,9]-15βH,3'H-cycloprop[14,15]-estra-1,3,5(10)-trien-3-ol;

and a pharmaceutically acceptable carrier and/or diluent;

wherein said steroid compound has a selective neurotropic transcription action in contrast to a systemic action like that of estrogens.

6. The method according to claim 5, wherein said effective amount is from 0.05 to 2 µg and said administering occurs once a day.

7. A method of treating estrogen deficiency in the central nervous system of a man or an animal, said method comprising administering an effective amount of 15βH,3'H-cycloprop[14,15]-estra-1,3,5(10),8-tetraen-3,17α-diol.

8. The method according to claim 7, wherein said effective amount is from 0.05 to 2 µg and said administering occurs once a day.

* * * * *